United States Patent
Cathier et al.

(10) Patent No.: US 9,142,015 B2
(45) Date of Patent: Sep. 22, 2015

(54) MEDICAL IMAGING SYSTEM AND METHOD FOR PROVIDING AN IMAGE REPRESENTATION SUPPORTING ACCURATE GUIDANCE OF AN INTERVENTION DEVICE IN A VESSEL INTERVENTION PROCEDURE

(75) Inventors: Pascal Yves Francois Cathier, Asnieres-sur-Seine (FR); Raoul Florent, Rueil-Malmaison (FR)

(73) Assignee: Koninklijke Philips N.V., Eindhoven (NL)

( * ) Notice: Subject to any disclaimer, the term of this patent is extended or adjusted under 35 U.S.C. 154(b) by 85 days.

(21) Appl. No.: 14/002,373

(22) PCT Filed: Feb. 24, 2012

(86) PCT No.: PCT/IB2012/050855
§ 371 (c)(1),
(2), (4) Date: Aug. 30, 2013

(87) PCT Pub. No.: WO2012/117321
PCT Pub. Date: Sep. 7, 2012

(65) Prior Publication Data
US 2014/0023250 A1 Jan. 23, 2014

(30) Foreign Application Priority Data
Mar. 2, 2011 (EP) .................................... 11305223

(51) Int. Cl.
*G06K 9/00* (2006.01)
*G06T 7/00* (2006.01)
(Continued)

(52) U.S. Cl.
CPC ............... *G06T 7/0012* (2013.01); *A61B 6/032* (2013.01); *A61B 6/12* (2013.01); *A61B 6/4441* (2013.01);
(Continued)

(58) Field of Classification Search
None
See application file for complete search history.

(56) References Cited

U.S. PATENT DOCUMENTS

| 6,195,445 B1 * | 2/2001 | Dubuisson-Jolly et al. .. 382/107 |
| 2003/0236466 A1 | 12/2003 | Tarjan |
| 2005/0074154 A1 | 4/2005 | Georgescu |
| 2006/0079759 A1 | 4/2006 | Vaillant |

(Continued)

FOREIGN PATENT DOCUMENTS

WO WO2008107814 A1 9/2008

OTHER PUBLICATIONS

Brost A et al: "Respiratory Motion Compensation by Model-Based Catheter Tracking during EP Procedures", Medical Image Analysis, Oxford University Press, Oxofrd, GB., vol. 14, No. 5, Oct. 1, 2010, pp. 695-706, XP027153806.
Siemens A.G. et al., "2D Coronary Roadmap Overlaid on 2D Fluoroscopic Image", IP.COm Journal, IP.COm Inc., West Henrietta, NY, US, Apr. 24, 2010, XP013137741.

(Continued)

*Primary Examiner* — Bhavesh Mehta
*Assistant Examiner* — Feng Niu

(57) ABSTRACT

The present invention relates to visualizing information of an object. In order to provide spatial information and in addition situation specific data to the user while ensuring an effective perceptibility, a method (110) is provided comprising the steps of: a) providing (112) pre-navigation data (114) of a region of interest of an object (22); wherein the pre-navigation data comprises spatial geometrical data (116) and a functional parameter surface (118) in correspondence to the spatial geometrical data; b) acquiring (120) live image data (122) of the region of interest; c) detecting (124) an element (126) in the live image data; d) determining (128) spatial relation (130) of the pre-navigation data and the live image data; e) determining (132) the position (134) of the detected element in the spatial geometrical data, which determining is based on the spatial relation, and computing (136) a predetermined related point of location (138) on the functional parameter surface; f) generating (140) a combination (142) of a simplified surface representation (144) of the region of interest, which simplified surface representation is based on a visualization of the functional parameter surface, and a marker (146) indicating the computed predetermined related point of location; and g) displaying (148) the combination as navigation guidance (150).

21 Claims, 5 Drawing Sheets

(51) Int. Cl.
*A61B 6/00* (2006.01)
*G06T 7/20* (2006.01)
*A61B 6/03* (2006.01)
*A61B 6/12* (2006.01)

(52) U.S. Cl.
CPC ............... *A61B 6/487* (2013.01); *A61B 6/503* (2013.01); *A61B 6/5247* (2013.01); *A61B 6/5264* (2013.01); *A61B 6/5288* (2013.01); *G06T 7/0024* (2013.01); *G06T 7/2033* (2013.01); *G06T 2207/10072* (2013.01); *G06T 2207/10121* (2013.01); *G06T 2207/30021* (2013.01); *G06T 2207/30048* (2013.01); *G06T 2207/30101* (2013.01)

(56) References Cited

U.S. PATENT DOCUMENTS

| | | |
|---|---|---|
| 2009/0163800 A1 | 6/2009 | Xu |
| 2010/0048998 A1 | 2/2010 | Younge |
| 2010/0145193 A1* | 6/2010 | Florent et al. ............... 600/427 |
| 2010/0217116 A1 | 8/2010 | Eck |

OTHER PUBLICATIONS

Bebek 0 et al: "Model Based Control Algorithms for Robotic Assisted Beating Heart Surgery", Conference Proceedings. Annual International Conference of the IEEE Engineering in Medicine and Biology Society (IEEE Cat. No. 06CH37748); Aug. 30-Sep. 3, 2006; New York, NY, USA, IEEE, Piscataway, NJ, USA, Aug. 30, 2006, pp. 823-828, XP031389974.

* cited by examiner

MEDICAL IMAGING SYSTEM AND METHOD FOR PROVIDING AN IMAGE REPRESENTATION SUPPORTING ACCURATE GUIDANCE OF AN INTERVENTION DEVICE IN A VESSEL INTERVENTION PROCEDURE

CROSS-REFERENCE TO PRIOR APPLICATIONS

This application is the U.S. National Phase application under 35 U.S.C. §371 of International Application Serial No. PCT/IB2012/050855, filed on Feb. 24, 2012, which claims the benefit of European Application Serial No. 11305223.7, filed on Mar. 2, 2011. These applications are hereby incorporated by reference herein.

FIELD OF THE INVENTION

The present invention relates to a medical imaging system and a method for providing an image representation supporting accurate guidance of an intervention device in a vessel intervention procedure, especially suitable for fluoroscopy guided interventions, e.g. atrial fibrillation ablation procedures.

BACKGROUND OF THE INVENTION

Electrophysiology is a specific domain of interventional cardiology where physicians use intra-cardiac catheters to locate and cure electrical dysfunctions of the heart rhythm, under X-Ray fluoroscopy guidance. A challenging electrophysiology procedure is radio-frequency ablation for the treatment of atrial fibrillation. Electrophysiologists need a special training to perfectly know the anatomy and the access pathways to all the sites of interest and some practice to select the correct devices and manipulate them to the desired target. The patient's anatomy can be recorded with 3D imaging devices, e.g. through CT or MRI, or by injecting contrast agent locally just at the beginning of the intervention, e.g. into the left atrium and ostium of the pulmonary veins for atrial fibrillation or into coronary veins and sinus for a cardiac resynchronization therapy. The physician basically has to perform a mental registration to navigate in the live fluoro images where the structural information is not visible anymore. For atrial fibrillation procedures, knowing the exact positions of the catheters when measuring electrical potentials is the key to find the sources that cause fibrillation, e.g. the ectopic foci or the reentry loop. Even more important is an anatomical mapping of the ablation sites in order to perform the desired ablation patterns, such as pulmonary vein isolation or roof line ablation in the left atrium.

Tracking a third-party object like an interventional tool or a visible anatomical landmark is mandatory in interventional X-ray if one wants to compensate the motion of an anatomy of interest, e.g. a heart chamber or the coronary sinus, if said organ is mostly invisible.

However, the relationship between the motion of a tracked intervention device and the part of the anatomy that is interesting for electrophysilogic intervention may be complex. In the chest area, for example, the motion of an intervention device is mostly induced by two factors, the heart beat and the breathing motion.

Since in the chest area these two distinct motion sources effect their surrounding differently, it may be considered necessary to separate these motion sources Known measures for the separation of different motion sources, which motion sources produce motions with distinct frequency bands, are based on filtering the overall motion of the tracked objects to recover the motion originating from either one of the source. However, filtering may result in lags that alter the quality of the motion compensation. Furthermore, the outcome of filtering may degrade quickly when the image rate of the fluoroscopy drops down.

Another known measure consists of using a temporal model of one (or several) of the motion sources. The temporal model(s) is (are) then fitted to the recorded motion. This may not be very flexible for coping with a huge motion variability, e.g. arrythmia of the cardiac or breathing motion.

SUMMARY OF THE INVENTION

Therefore there may be a need for a robust medical imaging system and method implementing an image representation of an anatomy of interest supporting an accurate guidance of an intervention device inserted into a vessel, which vessel is subject to an induced motion caused by at least two different motion sources. The robustness should address the variation in rhythm and to framerate.

Such need may be met with the subject-matter of the independent claims. Further embodiments of the invention are defined in the dependent claims.

According to an aspect of the present invention, a medical imaging system for providing an image representation of an anatomy of interest supporting the accurate guidance of an intervention device in a vessel intervention procedure is proposed. The medical imaging system is adapted to perform the following steps, preferably but not exclusively in the indicated order:

(i) acquiring a first sequence of images of the vessel region of interest with the intervention device inserted into the vessel region of interest during a time frame without a first motion of the patient;

(ii) detecting a first motion sequence of a periodic motion of the intervention device during a second motion cycle by analyzing the motion of the intervention device in the first sequence of acquired images;

(iii) creating a motion model of the intervention device solely induced by the second motion;

(iv) determining an operator defining the relationship between the first motion sequence of the intervention device and the second motion;

(iv) acquiring live images of the vessel region of interest with the intervention device inserted into the vessel region of interest of the patient;

(v) subtracting the motion of the intervention device induced by the second motion using the operator and determining the motion of the intervention device induced by the first motion of the patient; and (vi) registering of a representation of the object of interest based on the first motion.

According to the invention the state of the different sources of motion present e.g. as a cardiac motion and a respirating motion, is recovered by assessing the actual shape of art intervention device, realized as one or several third party objects, and deducing the pose of another object of interest, typically a heart chamber, based on the relevant motion.

At the heart of the invention is the assumption that different sources of motion deform the shape of an intervention device in different ways, so that the respective influence of these sources on the motion can be recovered unambiguously. With the help of one or several motion models, the motion induced by the different factors can then be inferred and propagated to other objects such as the anatomy of interest. By contrast to the existing techniques, a key benefit of this approach is the lack of dependency of the results to the framerate, and its ability to produce an estimate of the position of the anatomy of interest without time lag.

The acquisition of the first set of images of the anatomy region of interest may be conducted by an X-ray imaging apparatus that is able to provide a series of subsequent 2D-images. The intervention device may comprise one or several distinguishing features or landmarks that are feasible for recognition in an X-ray image for the purpose of defining a model of the intervention device and further for detecting a first motion sequence of a motion of the intervention device induced by a second motion source, which may be cyclic but not necessarily periodic, e.g. a cardiac motion. The definition of the model for the intervention device may be conducted by a regression or other applicable methods.

For the definition of a relationship between the second motion source influencing the shape of the intervention device and the state of the intervention device itself the definition of a motion model is mandatory. Such a motion model may be set up as a matrix or a vector that may be multiplied by a first motion source vector, such as a first motion scalar, e.g. a radian value of a recurring motion, for achieving a position vector describing the position of the intervention device depending on the state of the first motion source. In general, the motion model takes the shape of the interventional device as an input and outputs a phase or a displacement either through analytically or experimentally determined relationship. The input should preferably not be a derivative such as a velocity, since in the most basic mode the motion model should be usable based on a single frame. Furthermore, in low framerate sequences a velocity can hardly be estimated.

The determination of an operator as a reversed motion model may be conducted by transposing the motion model of the intervention device through a convenient transposition function depending on the nature of the motion model and its dimensionality.

An acquisition of live fluoroscopy images of the anatomy region of interest with the intervention device inserted into the anatomy region of interest is necessary for making the intervention device visible, which intervention device is to be guided to a certain spot such as the left atrium. It is pointed out that the live images may be acquired without restrictions regarding the motion of the patient.

In a following step a motion model of the intervention device based on the first motion source only, e.g. a respirating motion, is conducted by analyzing the motion of the intervention device according to the first learning step in which the shape deformations are only induced by the second motion source. When the shape of the intervention device is monitored under the influence of both second motion source and first motion source the shape deformation of the intervention device induced by the second motion source may be subtracted under utilization of the operator as the reversed motion model described above. Thereby, a motion model as a relationship between the first motion source and the motion of the intervention device may be gained.

This relationship helps in registering of a previously acquired image of the anatomy of interest and the live fluoroscopy images based on especially the respirating motion. This may be helpful, since e.g. the motion of the left atrium substantially does not depend on the second motion source, especially the cardiac motion, but is rigidly moved under the influence of the respiration.

In a formalized manner there are $n_s$ sources and $n_o$ objects that are tracked along time. Each source and object is unambiguously described by its state, which is noted respectively $S_i$, and $T_i$ and which may or may not be multidimensional. In the following it is assumed that the states $T_i$ of the objects depend on the states of the motions sources $S_i$ only, that is, $$T_i = \hat{T}_i(S_1, \ldots, S_{n_s}),$$

where $\hat{T}_i$ represents a motion model. It is further assumed that this action is reversable with the knowledge of the state of all objects, i.e. that for each source, there is an operator such that $$H_i(T_1, \ldots, T_{n_O}) = S_i.$$

The state A of an object of interest, assuming again that it depends on the $S_i$ only, is then recovered by $$A = \hat{A}(S_1, \ldots, S_{n_s}) = \hat{A}(H_1(T_1, \ldots, T_{n_O}), \ldots H_{n_s}(T_1, \ldots, T_{n_O})),$$

assuming a motion model $\hat{A}$. It may be possible that the anatomy of interest itself is counted in the interventional devices if its observable state is somehow insufficient and needs to be augmented by the observation of other intervention devices or other third party object.

The learning of the models is necessarily specific to the application. Models may either be universally applicable or need patient-specific learning.

The proposed medical imaging system may be applied in X-ray catheterization laboratory systems as used potentially in an operation room environment. Furthermore, it may also be exploited in other situations where guidance support may be meaningful. Other applications where this invention can be used are minimal invasive surgery where locating interventional instruments such as biopsy needles is of high interest.

According to a further aspect of the present invention, a computer program or a computer program element is proposed that is characterized by being adapted to execute the method steps as defined above with respect to the proposed medical imaging device when executed on an appropriate computing device or programmable system. In fact, a computing device or programmable system on which such computer program is executed and which furthermore comprises for example suitable interfaces, processors and memory for acquiring the respective anatomy representation data and X-ray image data as an input for subsequent data processing for providing the anatomy-angiogram-registration, the angiogram-fluoroscopy-registration and finally the anatomy-fluoroscopy-registration, may be operative as the above-defined medical imaging device.

According to a further aspect of the present invention, a computer-readable medium such as a CD-ROM is presented wherein the computer-readable medium has a computer program as described in the preceding section stored thereon. However, the computer program may also be presented over a network and may be downloaded into the working memory of a data processor from such network. Accordingly, the computer-readable medium may be a medium for making a computer program available for downloading.

It has to be noted that features and advantages of embodiments of the invention are described herein with reference to different subject-matters. In particular, some embodiments are described with respect to method type features whereas other embodiments are described with respect to device type features. However, a person skilled in the art will gather from the above and the following description that, unless otherwise notified, in addition to any combination of features belonging to one type of subject-matter also any combination between features relating to different subject-matters is considered to be disclosed with this application. Particularly, features can be combined providing synergic effects that are more than the simple sum of the features.

BRIEF DESCRIPTION OF THE DRAWINGS

The features and embodiments defined above and further features and advantages of the present invention can also be derived from the examples of embodiments to be described herein after and are explained with reference to examples of embodiments, but to which the invention is not limited. The invention will be described in more detail hereinafter with reference to the drawings.

The figures are only schematically and not to scale.

DETAILED DESCRIPTION OF EMBODIMENTS

Figure 1:
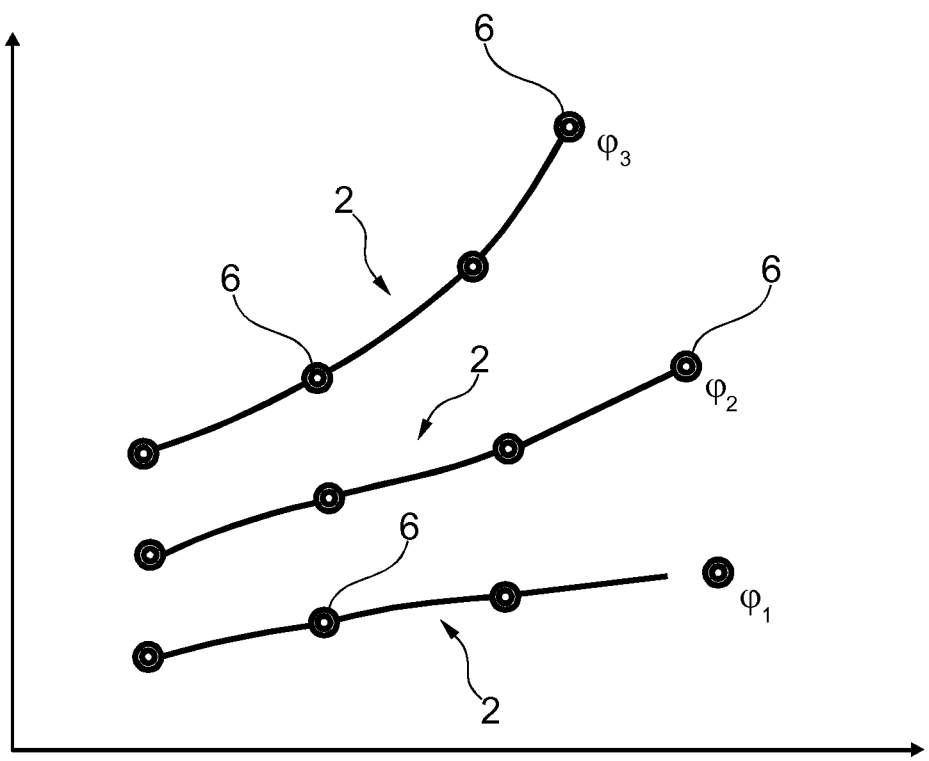
FIG. 1 shows an overview of shape deformations of an intervention device during a complete cardiac cycle.

FIG. 1 shows an overview of shape deformations of an intervention device during a complete cardiac cycle. An intervention device 2 is shown for three different phases $\phi_1$, $\phi_2$ and $\phi_3$ of a cardiac cycle, wherein two of these phases may be achieved by end of diastolic (EoD) and end of systolic (EoS) timed triggering. The intervention device 2 may be realized as a coronary sinus catheter (CSC) that is commonly used for occlusion of the coronary sinus, for dispensing cardioplegic solutions and also for monitoring the pressure of the coronary sinus during cardiopulmonary bypass surgery. For electrophysiology applications the coronary sinus catheter comprises electrodes 6 at its tip that may be used as clearly visible landmarks for the shape deformation to which the shape of the intervention device may be reduced.

The three different shape deformations in FIG. 1 are recorded during at least one cardiac cycle when the patient is not conducting a respirating motion. An instance of a cardiac cycle can automatically be detected by analyzing the motion of the intervention device 2 as it basically conducts a recurring motion. The state of the heart during a cardiac cycle may be represented by a variable S $\epsilon[0, 2\pi]$ since the motion is cyclic. Furthermore, this state may be proportional to time.

The determination of the relationship between the shape deformation and the cardiac cycle, or the displacement at the cardiac cycle, is a key of the proposed system and method as the respirating motion is assumed to rigidly affect the intervention device 2. The shape deformation induced by the cardiac cycle and the respirating motion are superposed and may only be separated through the isolated determination of cardiac cycle induced motion of the intervention device. The operator H giving the state S from the shape of the intervention device 2 may be determined for example by regression techniques on the detected cardiac cycle using various shape features of the intervention device 2, such as orientation, curvature, or the relative position of the electrodes.

If it is possible to obtain a three-dimensional position of the electrodes from their two-dimensional projections, e.g. using an anatomic shape prior and a three-dimensional model of the intervention device, a three-dimensional position of the electrodes 6 as the state of the intervention device 2 throughout the heart cycle may be learned. Otherwise, the state may be limited to a two-dimensional position of the electrodes 6, and the model may only be valid until a C-arm of a medical imaging system according to the invention is rotated.

This process may be considered a "learning phase" during which a motion model defining the relationship between intervention device shape deformations and the cardiac cycle is conducted. Thereby, knowing the position within a cardiac cycle, the shape deformation of the intervention device may be determined precisely.

Figure 2:
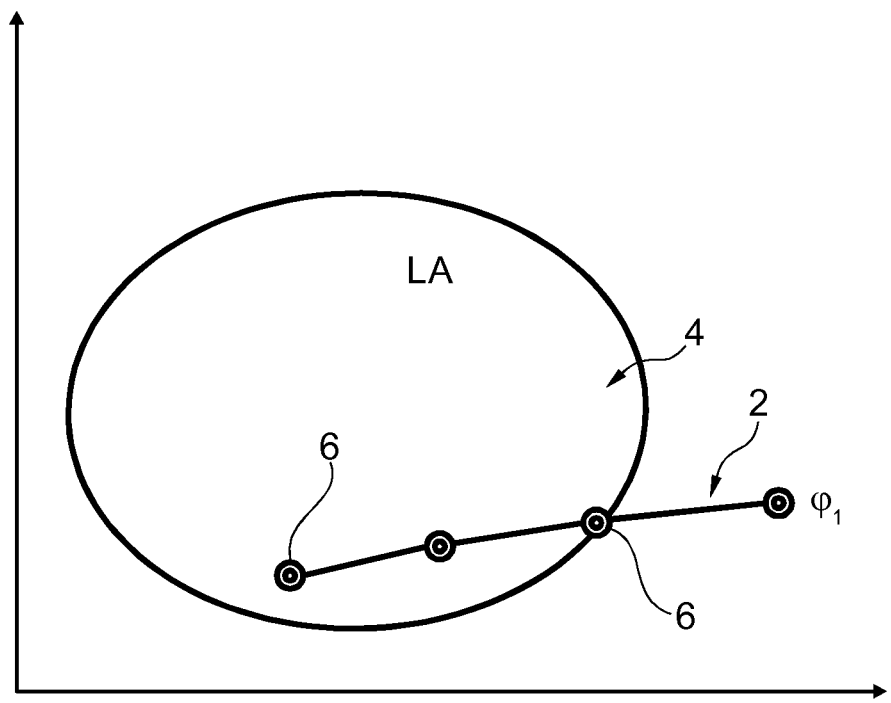
FIG. 2 shows a position of an anatomy of interest relative to the intervention device at a given phase.

In FIG. 2 a schematic overview of the anatomy of interest is shown. Here, the anatomy of interest is a left atrium (LA) 4. The two main sources of motion correspond to the heart beat (cardiac cycle) and the breathing (respirating motion). It is assumed that the respirating motion rigidly moves both the left atrium 4 and the intervention device 2, and that the heart beat does not affect the left atrium 4, which is a reasonable assumption near the roof of the left atrium 4, which is the main region of interest during ablation procedures.

The arrangement of the left atrium 4 and the intervention device 2 is given by the time the image has been acquired. For the image to be acquired a contrast agent may have been applied to the patient for the purpose of making the left atrium 4 visible in an X-ray image acquisition process. The contrast agent shows the anatomy of the left atrium 4, and therefore a model or a previously achieved image can be placed on a screen to the operator, either manually or automatically. To initialize the model in the same frame as the interventional device 2 only a single cardiac motion phase is needed to make an appropriate link. Useful phases for this task are the ones that are easy to detect automatically, showing extreme positions on the course of the intervention device, e.g. corresponding roughly to the EoD and EoS.

Exemplarily, the intervention device 2 has the position $\phi_1$ in FIG. 2. Since the position of the intervention device 2 relative to the left atrium 4 is known and the motion model of the intervention device 2 is determined, the position of the left atrium 4 is determinable for any occuring heart phase. Therefore, on a new image the shape of the intervention device 2 is analyzed, yielding the heart phase.

Using the motion model learned above the motion induced by the heart can be determined. A remaining rigid motion is then entirely attributed to the respirating motion, thus giving the breathing state, and in turn the position of the left atrium 4.

In its simplest form, the respirating motion is assumed to be a vertical translation applied uniformly to the intervention device 2 and the left atrium 4. The remaining translation of the intervention device 2 once the heart beat is factored out, can therefore directly be applied to the model of the left atrium 4.

Figure 3:
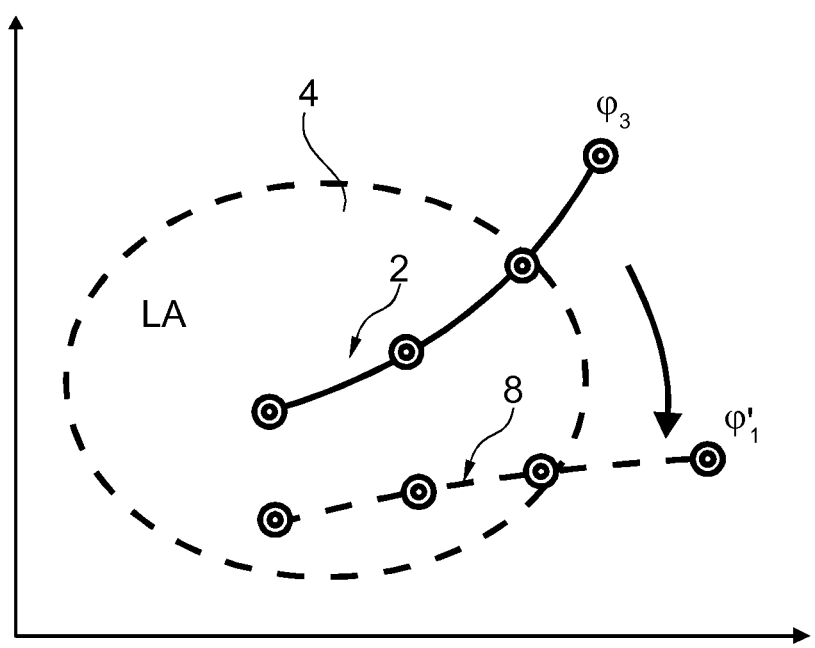
FIG. 3 shows an estimated position of an anatomy of interest relative to the intervention device at another phase.

Therefore, after having acquired the image of the left atrium 4 and having determined a motion model of the intervention device 2 the position of the left atrium 4 without contrast agent is determinable for all cardiac cycle phases and during a respirating motion. The relative position of the left atrium 4 can he made visible to the person conducting the intervention process in registering and superposing the previously acquired image of the left atrium 4 or a model of the left atrium 4 and live fluoroscopy images yielding the actual shape of the intervention device, as depicted in FIG. 3.

Thereby, the detected shape of the intervention device 2 under usage of the determined motion model from the learning phase as depicted in FIG. 1 enables to determine the relationship between a respirating motion and the relative position of the left atrium 4.

The motion correction may further be conducted through an estimation of the shape 8 of the intervention device 2 during the cardiac phase. For example, if the actual shape of the intervention device 2 equals the shape according to the phase $\phi_3$ of the cardiac cycle as depicted in FIG. 1 the corresponding shape of the intervention device 2 at the phase $\phi_1$ may be estimated by means of the motion model. This is indicated by an arrow pointing from the shape of the intervention device 2 at $\phi_3$ to the estimated shape at $\phi_1$ that may be named $\phi_1'$. This estimation may then be used to determine the position of the left atrium 4 as shown in FIG. 2.

Figure 4:
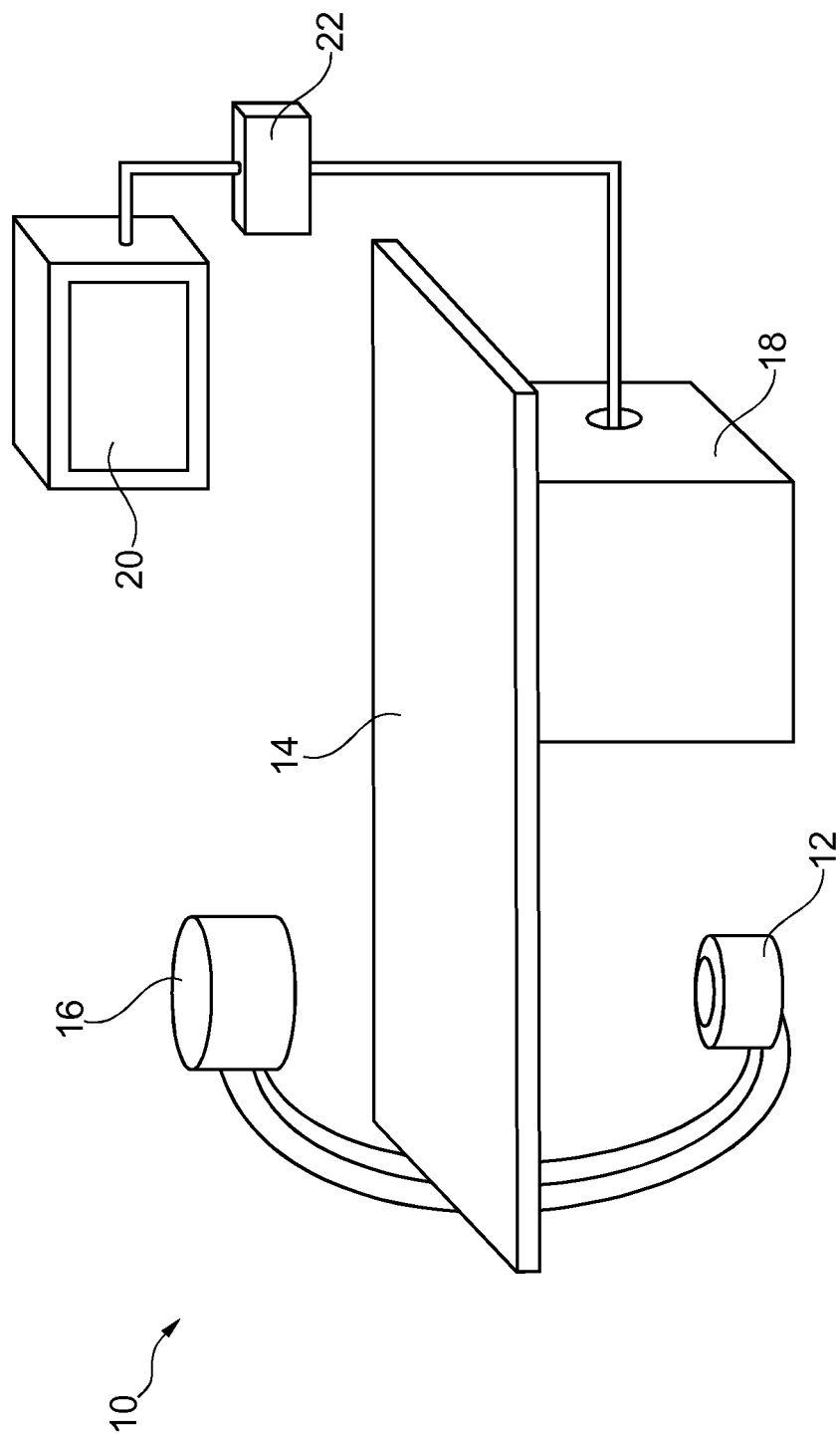
FIG. 4 shows an overview of a medical imaging system according to the invention.

FIG. 4 shows a diagrammatic overview of a medical imaging system according to the invention. The medical imaging system 10 comprises an X-ray image acquisition device with a source of X-ray radiation 12 provided to generate X-ray radiation. A table 14 is provided to receive an object to be examined. Further, an X-ray image detection module 16 is located opposite the source of X-ray radiation 12. During the radiation procedure, the examined object is located between the source of X-ray radiation 12 and the detection module 16. The latter sends data to a data processing unit 18, which is connected to both the X-ray image detection module 16 and the X-ray radiation source 12. The data processing unit 18 may exemplarily be located underneath the table 14 for saving space within the examination room. It is clear that it could also be located at a different place, such as in a different room or a different laboratory. Furthermore, an output unit 20 is exemplarily equipped with a display and therefore may be arranged in the vicinity of the table 14 for displacing information to the person operating the medical viewing system, which can be a clinician such as a cardiologist or a cardiac surgeon. Preferably, the display is movably mounted to allow for an individual adjustment depending on the examination situation. Also, an interface unit 22 is arranged to input information by the user.

It is not necessary to use a standalone output unit 20, it may also be possible to include the output unit 20 in the data processing unit 18, where an overlaying and combining process is conducted and provided at suitable output ports for further purposes.

Basically, the image detection module 16 generates images by exposing this subject to X-ray radiation, wherein said images are further processed in the data processing unit 18. It is noted that the example shown is of a so-called C-type X-ray image acquisition device. The X-ray image acquisition device comprises an arm in form of a C where the detection module 16 is arranged at one end of the C-arm and the source of X-ray radiation 12 is located at the opposite end of the C-arm. The C-arm is movably mounted and can be rotated around the object of interest located on the table 14. In other words, it is possible to acquire images with different directions of view.

The data processing unit 18 may be adapted to conduct the method according to the invention and thus can be considered as or comprise the data processing unit for providing an image representation supporting accurate guidance of an intervention device in a vessel intervention procedure. Thereby, a data processor and preferably a storage means for storing the motion model of the intervention device and the model of the object of interest is provided as well as a related software that leads one program element for providing an image representation supporting accurate guidance of an intervention device in a vessel intervention procedure according to exemplary embodiments of the above-described method. The software can be transferred into the data processing unit 18 by means of a computer-readable medium or through a network and may be realized as a complete new operating system or an update.

Figure 5:
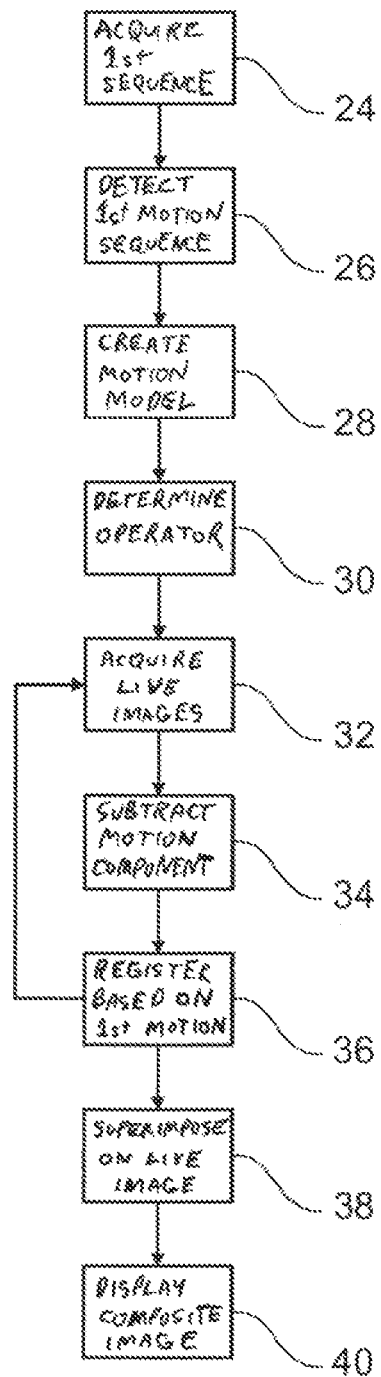
FIG. 5 shows a diagrammatic overview of a method according to the invention.

As becoming apparent in FIG. 5 the method according to the present invention comprises the following process steps:

(i) acquiring 24 a first sequence of images of the vessel region of interest with the intervention device 2 inserted into the vessel region of interest during a time frame without a first motion of the patient;

(ii) detecting 26 a first motion sequence of a cyclic motion of the intervention device 2 during a second motion cycle by analyzing the motion of the intervention device 2 in the first sequence of acquired images;

(iii) creating 28 a motion model of the intervention device solely induced by the second motion;

(iv) determining 30 an operator defining the relationship between the first motion sequence of the intervention device 2 and the second motion;

(iv) acquiring 32 live images of the vessel region of interest with the intervention device 2 inserted into the vessel region of interest;

(v) subtracting 34 the motion of the intervention device induced by the second motion using the operator and determining the motion of the intervention device 2 induced by the first motion; and (vi) registering 36 of a representation of an object of interest based on the first motion.

It is pointed out that the live images may be acquired without restrictions regarding the motion of the patient.

The registered representation of the object of interest may furthermore be superposed 38 to the acquired live image and displayed 40.

Finally, it is to be noted that herein the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

LIST OF REFERENCE SIGNS:

2 intervention device
4 left atrium (LA)
6 electrode
8 shape
10 medical imaging system
12 source of X-ray radiation
14 table
16 detection module
18 data processing unit
20 standalone output unit
22 interface unit
24 acquiring a first sequence of images
26 detecting a first motion sequence
28 creating a motion model
30 determining an operator
32 acquiring live images
34 subtracting motion of the intervention device
36 registering of a representation of an object of interest
38 superposing
40 displaying

The invention claimed is:

1. A circuit for providing an image representation supporting accurate guidance of an intervention device in a vessel intervention procedure in a region of interest of a patient, in which region a position of an object of interest is depending on at least a first source of motion, said circuit being configured for performing a plurality of acts, from among said plurality there being the acts of:

(i) acquiring a first sequence of images of said region of interest with the intervention device inserted into said region of interest during a time frame without a first motion of the patient;

(ii) detecting a first motion sequence of a periodic motion of the intervention device during a cycle of second motion by analyzing motion of the intervention device in the first sequence of acquired images;

(iii) creating a motion model representative of motion, of the intervention device, that is solely induced by the second motion;

(iv) determining an operator (H) defining a relationship between said first motion sequence and the second motion;

(v) acquiring live images of said region of interest with the intervention device inserted into said region of interest;

(vi) subtracting said solely induced motion using the operator (H) and determining the motion of the intervention device induced by the first motion of the patient; and (vii) registering of a previously acquired image of an object of interest based on the first motion.

2. A medical imaging system comprising the circuit of claim 1 and a medical image acquisition device operable by said circuit for said acquiring of acts (i) and (v).

3. The system of claim 2, wherein the first motion source is a respirating motion.

4. The system of claim 2, wherein the second motion source is a cardiac motion.

5. The system of claim 2, wherein the region of interest is a region surrounding an aortic root.

6. The system according to claim 2, wherein the object of interest is a left atrium.

7. The system of claim 2, further being adapted for superposing the representation of the object of interest onto the live images and displaying the resulting images onto a screen.

8. The system of claim 2, wherein said medical image acquisition device comprises an X-ray imaging apparatus.

9. A data processing unit comprising a data processor, said data processor comprising the circuit of claim 1.

10. A medical imaging system comprising the circuit of claim 1 and a medical image acquisition device operable by said circuit for said acquiring of acts (i) and (v).

11. The circuit of claim 1, wherein said subtracting of act (vi) operates on live imaging acquired in act (v).

12. A medical imaging system comprising the circuit of claim 11 and a medical image acquisition device operable by said circuit for said acquiring of acts (i) and (v).

13. The circuit of claim 11, wherein said using of act (vi) entails using output of said operator (H) in deriving a subtrahend for said subtracting.

14. The circuit of claim 1, wherein said using of act (vi) entails using output of said operator (H) in deriving a subtrahend for said subtracting.

15. The circuit of claim 1, wherein from among said plurality of acts there being the further act of, prior to the acquiring of an image from among said live images in act (v), acquiring an image as said previously acquired image.

16. The circuit of claim 15, wherein said registering entails registering to the acquired live image.

17. The circuit of claim 1, said determining of said motion resulting from said subtracting.

18. A method for providing an image representation supporting accurate guidance of an intervention device in a vessel intervention procedure in a region of interest of a patient, in which region a position of an object of interest is depending on at least a first source of motion, the method comprising:

(i) acquiring a first sequence of images of said region of interest with the intervention device inserted into said region of interest during a time frame without a first motion of the patient;

(ii) detecting a first motion sequence of a periodic motion of the intervention device during a cycle of second motion by analyzing motion of the intervention device in the first sequence of acquired images;

(iii) creating a motion model representative of motion, of the intervention device, that is solely induced by the second motion;

(iv) determining an operator (H) defining a relationship between said first motion sequence and the second motion;

(v) acquiring live images of said region of interest with the intervention device inserted into said region of interest;

(vi) subtracting said solely induced motion using the operator (H) and determining the motion of the intervention device induced by the first motion of the patient; and (vii) registering of a previously acquired image of an object of interest based on the first motion.

19. A non-transitory computer-readable medium embodying a computer program for providing an image representation supporting accurate guidance of an intervention device in a vessel intervention procedure in a region of interest of a patient, said computer program having instructions executable by a processor for performing a plurality of acts, from among said plurality there being the acts of:

(i) acquiring a first sequence of images of said region of interest with the intervention device inserted into said region of interest during a time frame without a first motion of the patient;

(ii) detecting a first motion sequence of a periodic motion of the intervention device during a cycle of second motion by analyzing motion of the intervention device in the first sequence of acquired images;

(iii) creating a motion model representative of motion, of the intervention device, that is solely induced by the second motion;

(iv) determining an operator (H) defining a relationship between said first motion sequence and the second motion;

(v) acquiring live images of said region of interest with the intervention device inserted into said region of interest;

(vi) subtracting said solely induced motion using the operator (H) and determining the motion of the intervention device induced by the first motion of the patient; and (vii) registering of a previously acquired image of an object of interest based on the first motion.

20. The computer readable medium of claim 19, wherein said subtracting of act (vi) operates on live imaging acquired in act (v).

21. The computer readable medium of claim 19, wherein said using of act (vi) entails using output of said operator (H) as a subtrahend in said subtracting.

* * * * *